United States Patent [19]

Yaginuma et al.

[11] Patent Number: 5,008,078

[45] Date of Patent: Apr. 16, 1991

[54] INTEGRAL MULTI-LAYER ANALYSIS ELEMENT

[75] Inventors: Nakatsugu Yaginuma; Takaki Arai, both of Saitama, Japan

[73] Assignee: Fuji Photo Film Co., Ltd., Kanagawa, Japan

[21] Appl. No.: 182,707

[22] Filed: Apr. 18, 1988

[30] Foreign Application Priority Data

Apr. 16, 1987 [JP] Japan .................................. 62-94138

[51] Int. Cl.$^5$ .............................................. G01N 31/22
[52] U.S. Cl. ........................................ 422/56; 422/57; 436/113; 436/170
[58] Field of Search ................... 422/56, 57; 436/169, 436/170, 106, 108, 113

[56] References Cited

U.S. PATENT DOCUMENTS

| | | | |
|---|---|---|---|
| Re. 30,267 | 5/1980 | Bruschi | 422/57 |
| 3,901,657 | 8/1975 | Lightfoot | 422/56 |
| 3,992,158 | 11/1976 | Przybylowicz et al. | 422/58 |
| 4,166,093 | 8/1979 | Smith-Lewis et al. | 422/56 |
| 4,548,906 | 10/1985 | Sekikawa et al. | 422/56 |
| 4,719,085 | 1/1988 | Jacobs | 436/113 |

FOREIGN PATENT DOCUMENTS

| | | |
|---|---|---|
| 0173276 | 3/1986 | European Pat. Off. . |
| 0204334 | 12/1986 | European Pat. Off. . |
| 2626367 | 12/1976 | Fed. Rep. of Germany . |
| 2085159 | 4/1982 | United Kingdom .................. 422/56 |
| 2102568 | 2/1983 | United Kingdom . |

OTHER PUBLICATIONS

European Search Report.

*Primary Examiner*—Robert J. Warden
*Assistant Examiner*—Lyle Alfandary-Alexander
*Attorney, Agent, or Firm*—Sughrue, Mion, Zinn Macpeak & Seas

[57] ABSTRACT

A multi-layer analysis element including an endogenous ammonia trapping layer, an ammonia producing layer containing a composition capable of reacting with an ammonia producing substance to produce gaseous ammonia, and at least one layer essentially incapable of trapping ammonia and essentially incapable of producing ammonia, and capable of preventing the diffusion of ammonia, disposed between the endogenous ammonia trapping layer and the ammonia producing layer. The unified multi-layer analysis element according to the invention is useful for the quantitative analysis of ammonia producing substances in aqueous biological food samples, with a high degree of sensitivity and accuracy, using a simple procedure.

7 Claims, No Drawings

INTEGRAL MULTI-LAYER ANALYSIS ELEMENT

FIELD OF THE INVENTION

This invention concerns integral multi-layer analysis elements for the analysis of substances which can produce ammonia in a liquid sample as the analyte. More particularly, the invention concerns integral multi-layer type analysis elements which are suitable for the quantitative analysis of ammonia producing substances such as creatinine and urea etc. which are contained in biological fluids such as blood, urine, lymph etc., without being affected by endogenous ammonia.

BACKGROUND OF THE INVENTION

The quantitative analysis of ammonia producing substances such as creatinine and urea etc. which are contained in biological fluids is of the utmost importance in the diagnosis of diseases such as kidney disease, in examinations carried out for controlling the course of such diseases and in the examination of kidney function.

Method of analysis by a procedure in which ammonia is produced from an ammonia producing substance and a procedure in which the ammonia so produced is determined are typical of the methods used for the analysis of ammonia producing substances. Such methods of analysis involving conversion to ammonia used on a wide scale in the past include wet methods or solution methods. Moreover, in recent years, dry methods of analysis based on conversion to ammonia in which dry analytical devices as typified by the integral multi layer analytical element are used, have been proposed and put into practice.

The above mentioned procedures for producing ammonia from ammonia producing substances generally involve methods in which the ammonia is generated by the action of an enzyme. For example, methods in which the creatinine in a liquid sample is hydrolyzed specifically to ammonia and N-methylhydantoin by means of creatinine deiminase (EC3.5.4.21) can be used for the quantitative analysis of creatinine in a biological fluid. Furthermore, methods in which urea is hydrolyzed to ammonia and carbon dioxide using urease as a catalyst can be used for the quantitative analysis of urea nitrogen in biological fluids (referred to below as BUN). In these methods the ammonia producing substance, which is the analyte, is the substrate of an enzyme and so they are known as ammonia generating substrates. Methods for the analysis of these ammonia generating substances have been disclosed in *Analytical chemistry*, 46, 246 (1974), *Clinica Chimica Acta*, 18, 409 (1967), *Clinical Chemical Analysis III, Nitrogen Containing Components* (Japanese) pages 13-14 and pages 67-87 (Tokyo Kagaku Dojin, Tokyo, 1979) and *Journal of Medical Technology* (Japanese, Vol. 5 (No. 6), pages 387-391 (1961) etc.

However, the biological fluids which are these analytes often contain ammonia (endogenous ammonia) in a state in which it has been released as ammonium ions, and it has not been possible to disregards the errors which have arisen as a result of the presence of this endogenous ammonia. Hence it is necessary to eliminate the effect of the endogenous ammonia in order to determine the quantity of the ammonia producing substrates precisely, and some methods for the elimination of endogenous ammonia have already been proposed.

Actual examples of methods for the analysis of ammonia producing substances which include a procedure for the pre-elimination of endogenous ammonia in a wet method include the quantitative methods disclosed in Japanese Patent Application (OPI) Nos. 5,198/83 corresponding to GB 2102 568A, 21,398/84, 31,696/84, 31,697/84, 31,698/84, 31,700/84 and 56,095/86 corresponding to EP 0173 276A etc. (the term "OPI" as used herein refers to a "published unexamined Japanese patent application").

Integral multi-layer analysis elements for the analysis of ammonia producing substances in which the effect of the endogenous ammonia is eliminated (or abated) by an endogenous ammonia trapping function within the analysis element itself, such as the integral multi-layer elements disclosed in Japanese Patent Application (OPI) No. 278,761/86 corresponding to EP 0204 334A, have also been disclosed as dry methods of analysis. These multi-layer analysis elements have an endogenous ammonia trapping layer, in which an ammonia trapping reaction takes place, established adjacent to and above the layer in which ammonia is formed by the ammonia producing reaction.

More, reagent compositions which contain an enzyme which converts ammonia as substrate to another substance are included in the endogenous ammonia trapping layer. Actual examples of such compositions include those which contain NADH (the reduced form of nicotinamide adenine dinucleotide) and/or NADPH (the reduced form of nicotinamide adenine dinucleotide phosphate), glutamic acid dehydrogenase (EC1.4.1.3) and $\alpha$-ketoglutaric acid (or a salt thereof).

It is evident that because the endogenous ammonia trapping layer is adjacent to the reaction layer in which the ammonia producing reaction takes place, in integral multi-layer analysis elements for the analysis of ammonia producing substances which have an endogenous ammonia trapping layer, the measurement sensitivity has tended to be lower than that of an element in which no endogenous ammonia trapping layer is used, since ammonia which has been produced by the ammonia generating reaction diffuses upwards and takes part in a side reaction in the endogenous ammonia trapping layer.

SUMMARY OF THE INVENTION

One object of this invention is to provide integral multi-layer analysis elements for the quantitative analysis of ammonia producing substances in which measurement errors due to ammonia (endogenous ammonia) which is present in an aqueous fluid sample are eliminated and with which the analysis can be carried out with a high degree of sensitivity.

A further object of the invention is to provide integral multi-layer analysis elements with which ammonia producing substances such as creatinine and blood urea nitrogen (hereinafter refer to "BUN") can be analyzed quantitatively with a high level of accuracy and quickly, using a simple procedure.

It has now been discovered that these and other objects of the present invention can be attained by a multi-layer analysis element including an endogenous ammonia trapping layer, an ammonia producing layer, containing a composition capable of reacting with an ammonia producing substance to produce gaseous ammonia, and at least one layer essentially incapable of trapping ammonia and essentiallY incapable of producing ammonia and capable of preventing the diffusion of gaseous ammonia, disposed between the endogenous ammonia trapping layer and the ammonia producing layer.

DETAILED DESCRIPTION OF THE INVENTION

Preferred embodiments of the invention include the following structures:

[1] Multi-layer analysis elements for the quantitative analysis of ammonia producing substances in which there are laminated sequentially:
(1) An optically transparent and water impermeable support;
(2) An ammonia indicator layer which contains an indicator in which a detectable change is produced by gaseous ammonia;
(3) A liquid permeation barrier layer through which gaseous ammonia is able to pass;
(4) An ammonia producing reaction reagent layer which contains a reagent composition which reacts with ammonia producing substances and produces gaseous ammonia;
(5) A layer which essentially has no ammonia trapping or ammonia producing reaction function, but which has the function of essentially preventing the diffusion of gaseous ammonia;
(6) An endogenous ammonia trapping layer which contains a reagent composition which acts upon ammonia which is present in the aqueous fluid sample and converts this ammonia into a form in which it is unable essentially to reach the reaction reagent layer; and
(7) A porous spreading layer.

[2] Multi-layer analysis elements for the quantitative analysis of ammonia producing substances in which there are laminated sequentially:
(1) An optically transparent and water impermeable support;
(2) An ammonia indicator layer which contains an indicator in which a detectable change produced by gaseous ammonia;
(3) A liquid permeation barrier layer through which gaseous ammonia is able to pass;
(4) An ammonia producing reaction reagent layer which contains a reagent composition which reacts with ammonia producing substances and produces gaseous ammonia;
(5) A layer which essentially has no ammonia trapping or ammonia producing reaction function, but which has the function of essentially preventing the diffusion of gaseous ammonia; and
(6) A porous spreading layer which incorporates an endogenous ammonia trapping layer consisting of a porous layer which contains a reagent composition which acts upon the ammonia which is present in the aqueous fluid sample and converts the aforementioned ammonia into a form in which it is unable essentially to reach the above mentioned reaction reagent layer.

Other well-known layers such as intermediate layers, tacky intermediate layers, bonding layers and light shielding layers may also be included in the elements provided that they have no adverse effect on the function of the integral multi-layer analysis elements of this invention, as is described in EP 0204 334A.

As used herein, the term "ammonia producing substance" signifies a compound or group of compounds which react with a specific reagent and either produce ammonia themselves or produce ammonia by way of a number of reaction system. Furthermore, the layer which as the function of essentially preventing the diffusion of ammonia, without having an ammonia trapping or ammonia producing reaction function is referred to below as the "ammonia diffusion preventing layer".

The integral multi-layer analysis elements of this invention enable any endogenous ammonia to be trapped and removed in an upper layer, while the ammonia producing substance such as creatinine or BUN etc. is subsequently reacted in a reaction layer, and the ammonia which is formed produces any detectable change such as coloration in an indicator layer, thus being detected and quantified. The ammonia which is produced in the reaction layer is prevented from diffusion outward by the presence of the ammonia diffusion preventing layer, which is between the endogenous ammonia trapping layer and the ammonia producing reaction reagent layer, and thus the quantitative nature of the analysis of the ammonia producing substance is improved.

Hence, when the integral multi-layer analysis elements of this invention are used, there is no need to carry out complicated procedures such as determining the endogenous ammonia, or eliminating the endogenous ammonia in a pre-treatment or dialysis of the sample liquid, so the estimation of creatinine and urea etc. can be carried out easily and quickly. Furthermore, manipulation and handling are also simple since the analysis elements of this invention are integral element.

Moreover, the integral multi-layer analysis elements of this invention have a high sensitivity to ammonia producing substances and accurate analysis can be achieved even with fluid samples which contain only trace quantities of ammonia producing substances.

Furthermore, the integral multi-layer analysis elements of this invention are such that the ammonia producing substance is determined indirectly by reacting it (the analyte) with a reagent with which it reacts and produces ammonia and then determining the ammonia which is produced. Hence, by changing the type of the aforementioned reaction reagent for producing ammonia it is possible to make integral multi-layer analytical elements of this invention for the quantitative analysis of a variety of ammonia producing substances.

Specific examples of optically transparent and liquid impermeable supports (referred to below as supports) on which integral multi-layer analysis elements of this invention can be constructed include transparent supports made of transparent polymers such as polyethylene terephthalate, bisphenol A polycarbonate, polystyrene, or cellulose esters (for example cellulose diacetate, cellulose triacetate, cellulose acetate propionate etc.) having a thickness from about 50 $\mu$m to about 1 mm, and preferably from about 80 $\mu$m to about 300 $\mu$m.

An undercoating layer may be coated on the surface of the support as required in order to bond the reaction layer, or other layers (for example a water absorbing layer) more firmly onto the support. Furthermore, the strength of adhesion can be improved by subjecting the surface of the support to a physical or chemical treatment instead of providing an undercoating layer.

The ammonia indicator layer (referred to below as the "indicator layer") contains an indicator in which a detectable change is produced by gaseous ammonia. It is coated on the support, either directly or on another layer such as an undercoating layer etc., depending on the particular case. The indicator layer contains at least one type of color forming ammonia indicator. A color forming ammonia indicator is a compound in which a detectable change (for example a coloration or color change brought about by a change in the absorbing wavelength) is induced by gaseous ammonia.

Leuco dyes such as leuco cyanine dyes, nitro substituted leuco dyes and leuco phthalein dyes (as disclosed in Reissue U.S. Pat. No. 30,267 and Japanese Patent Application (OPI) No. 19,062/83): pH indicators such as bromophenol blues, bromocresol green, bromothymol blue, quinoline blue and rosolie acid etc. (described in "Chemical Dictionary" (Japanese) Vol. 10, pages 63-65 (published by Kyoritsu Shuppan Co.)): triarylmethane based dye precursors; leuco benzylidene dyes (disclosed in Japanese Patent Application (OPI) Nos. 379/80 and 145,273/81); diazonium salts and azo dye couplers; and base-bleachable dyes etc. can be used for the color forming ammonia indicator in an integral multi-layer analysis element of this invention.

The indicator layer is normally formed by preparing a coating liquid by mixing at least one of these color forming ammonia indicators with a polymer binder which is soluble in organic solvents or water and then coating this liquid onto the transparent support and drying. Specific examples of suitable polymer binders include, for example, cellulose esters such as cellulose monoacetate, cellulose diacetate, cellulose triacetate, cellulose acetate butyrate, cellulose acetate propionate etc. alkyl celluloses such as methylcellulose, ethylcellulose, propylcellulose etc. and synthetic vinyl polymers such as polymethylmethacrylate, polyacrylate, polystyrene, polyacrylonitrile, polyvinyl acetate, polyvinylbutyral, chlorinated polyvinyl acetate, polyacrylamide, polyvinyl pyrrolidone, polyvinylalcohol, or copolymers of these materials.

The amount of color forming ammonia indicator compounded is preferably within the range from about 1 wt% to about 20 wt% with respect to the weight of binder. Moreover, the pH of the indicator layer can be adjusted to within the range of the color forming pH of the color forming ammonia indicator by the addition to the indicator layer of an organic acid or an inorganic acid such as ethane sulfonic acid, asparaginic acid, azeleic acid, glutaric acid, succinic acid, glutaconic acid, tartaric acid, pimelic acid, malonic acid, malic acid, 3,3-dimethylglutaric acid, citric acid, p-toluene sulfonic acid, perchloric acid, hydrochloric acid etc., an organic base or an inorganic base such as aminomethane, aminoethane, ammonia, sodium hydroxide, potassium hydroxide, lithium hydroxide, etc, or pH buffers, in order to prevent any coloration or change in color of the color forming ammonia indicator during manufacture or storage.

The coating liquid with which the indicator layer is formed can be prepared by adding the color forming ammonia indicator, binder polymer and reagents, such as the above mentioned acids for pH adjustment which are added as required, to an organic solvent, such as acetone, 2-methoxyethanol, methyl ethyl ketone, dichloromethane, dichloroethane, methanol, ethanol etc., or water to provide a solid fraction concentration from about 1 wt% to about 30 wt%, and preferably from about 3 wt% to about 20 wt%. The coating liquid can be formed into an indicator layer by coating it onto the support and drying, normally in such a way that the layer thickness after drying is within the range from about 1 $\mu$m to about 30 $\mu$m, and preferably within the range from about 2 $\mu$m to about 20 $\mu$m.

A liquid permeation barrier layer (referred to below as the barrier layer) through which gaseous ammonia is able to pass is provided on top of the indicator layer. This barrier layer is a layer consisting of a substance through which gaseous ammonia is able to pass but through which liquids, such as coating liquids and sample fluids etc., or interfering components (for example alkaline components) which are contained in these liquids are essentially unable to pass or permeate, either during the manufacture of the multi-layer analysis element (in practical terms, during the coating of the reaction layer, which is described hereinafter, on the barrier layer) or during the analytical procedure.

Barrier layers can be broadly classified into two types from the structural point of view. The first type is an air barrier layer type (referred to below as an "air barrier layer") which consists of a porous material with connected pores in which a layer of air functions essentially as a barrier layer, and the second type is a polymer barrier layer type (referred to below as a "polymer barrier layer") consisting of a thin homogeneous, non-porous layer of hydrophobic polymer (or a polymer which has a low level of hydrophilicity).

Examples of porous materials which have connected pores which form an air barrier layer include membrane filters, porous materials in which fibrous materials have been entwined, stuck or bonded together (for example paper, filter paper, felt, non-woven cloths etc.), and porous materials consisting of a woven material base, a knitted material base or a fine mesh-like material.

Specific examples of membrane filters which can be used as air barrier layers include those made from cellulose acetate (cellulose diacetate or cellulose triacetate etc.) cellulose nitrate, regenerated cellulose, polyamides (nylons), bisphenol A polycarbonates, polyethylene, polypropylene and fluorine containing polymers such as polytetrafluoroethylene etc. When used in a integral multi-layer element of this invention, the thickness of the above mentioned membrane filters is within the range of about 30 $\mu$m to about 300 $\mu$m and preferably within the range from about 70 $\mu$m to 200 $\mu$m.

The porosity (void fraction) of the membrane filter is from about 25% to about 90% and preferably from about 60% to about 90%. Furthermore, the average pore size of the membrane filter is within the range from about 0.01 $\mu$m to about 20 $\mu$m and preferably within the range from about 0.1 $\mu$m to about 10 $\mu$m. Membrane filters which have the above mentioned characteristics can be manufactured using the methods disclosed in either U.S. Pat. No. 1,421,341 or Japanese Patent Application (OPI) No. 21,677/78, for example. Furthermore, a variety of suitable membrane filters is already available commercially from a number of manufactures and a membrane filter can be selected as required from among these products for use.

Porous materials consisting of fibrous materials which have been entwined, stuck or bonded together which can be used as air barrier layers in the invention are porous materials which have connected pores with a structure in which fibrous materials, such as those disclosed in Japanese Patent Application (OPI) No. 77,660/83, or aggregates thereof, are physically entwined or physically and/or chemically stuck or bonded together.

Specific examples of fibrous materials from which the above mentioned porous materials can be constructed include natural fibrous materials such as cellulose fibers, cotton fibers, hemp fibers, silk fibers, wool fibers etc., fibers consisting of regenerated or semisynthetic materials such as rayon fibers, vinylon fibers, cellulose acetate fibers etc., and fibrous materials consisting of synthetic materials such as glass wool, polyethylene fibers, polyethyleneterephthalate fibers, polyacrylonitrile fibrous materials and polyvinyl chloride fibers etc., or fibrous materials consisting of mixtures of such fibers. furthermore, examples of porous materials manufactured using the above mentioned fibrous materials include rice paper, Japanese papers such as "Minogami" and "Shojigami", papers such as filter paper, parchment paper, imitation parchment paper etc. which are made by subjecting fibrous materials to a papermaking process, and felts and non-woven cloths which have been made from fibrous materials.

The void fraction of the porous materials obtained by entwining, sticking or bonding together fibrous materials is normally within the range from about 20% to about 90% and preferably within the range from about 50% to about 85%. The average void size of the above mentioned porous materials is normally within the range of from about 0.01 $\mu$m to about 20 $\mu$m and preferably within the range from about 0.1 $\mu$m to about 10 $\mu$m. Furthermore, the thickness of the above mentioned porous materials is normally within the range from about 50 $\mu$m to about 500 $\mu$m and preferably within the range from about 70 $\mu$m to about 300 $\mu$m.

Examples of woven materials which can be used as air barrier layers include woven materials made from natural fibers (for example cotton broadcloths etc.), woven materials made from semi-synthetic fibers (for example broadcloths made from regenerated cellulose fibers such as viscose rayon, cuprammonium rayon, fortisan etc.), woven materials made from synthetic fibers (for example broadcloths made from fibers such as polyamides (nylon), and mixed woven materials consisting of natural fibers and semi-synthetic fibers or synthetic fibers (for examples broadcloths made from mixed spun yarns of cotton and polyethylene terephthalate fibers etc.). Examples of knitted materials which can be used as air barrier layers include knitted materials consisting of the same fibers, or yarns of the same fibers, as those which can be used in the manufacture of the aforementioned woven materials. Furthermore, examples of the fine mesh-like materials which can be used as air barrier layers include fine nets and fine meshes made of synthetic fibers or yarns (for example polyamides (nylons), polyethylene terephthalate, polyacrylonitrile, polyethylene, polypropylene, polyvinylchloride) etc. The thickness of the above mentioned woven, knitted or fine mesh like materials is normally within the range from about 30 $\mu$m to about 300 $\mu$m. Furthermore, the void fraction of the woven, knitted or mesh-like material is normally from about 20% to about 60% and preferably from about 40% to about 60%.

There is a danger that liquids, especially liquids which contain interfering substances such as alkaline materials in solution, will pass through the barrier layer as a result of a capillary action within the voids in the case of air barrier layers made of porous materials which have connected voids as described above. Hence the air barrier layer is preferably hydrophobic or water repellent to the extent that capillary flow due to the above mentioned capillary action does not occur. Furthermore, the application of a treatment to render the material hydrophobic or water repellent is preferred in cases where the porous material which has connected voids is only weakly hydrophobic or water repellent.

The above mentioned treatments for rendering the porous material hydrophobic or water repellent may be carried out by immersion in, coating with, or spraying with a known reagent for rendering materials hydrophobic or water repellent, as typified by the silicone resins, silicone oils, fluorinated resins and fluorinated oils, either in their original state or after dilution in a solvent (for example hexane, cyclohexane, petroleum ether etc.) as required to provide a solid content within the range from about 0.1 wt% to about 5 wt% and applying the reagents at least to the surface, or the vicinity of the surface, of the porous material which has connected voids.

The air barrier layer can be formed by attaching a porous material which has connected voids to the binder polymer which is soluble in organic solvents, or the water soluble binder polymer which forms the matrix for the indicator layer described earlier. The attachment of the porous material can be carried out by adhering the porous material while the indicator layer is wet and then drying the combination. In this context the statement "while the indicator layer is wet" signifies that the solvent in which the binder has been dissolved is still present, or that the dried film has been re-wetted with a dissolving solvent (an organic solvent or water), and that the binder which constitutes the matrix of the indicator layer is in a wet state, a dispersed state or in the form of a solution. Furthermore, in cases where the binder of the indicator layer is tacky, as in the case of polyvinyl acetate for example, the porous material which has connected voids can be adhered onto the indicator directly by the application of pressure, with no special wetting of the indicator layer.

Polymer barrier layers consisting of thin, homogeneous, non-porous layers of hydrophobic polymer (or a polymer which has limited hydrophilicity) are preferably made from hydrophobic polymers or polymers which have limited hydrophilicity. Specific examples of hydrophobic polymers and polymers which have limited hydrophilicity include cellulose acetate propionate, cellulose acetate butyrate, bisphenol A polycarbonate, polyethylene, polypropylene, ethylene-vinyl acetate copolymers, polyurethane, polystyrene, polyvinyl chloride, vinyl chloride-vinyl acetate copolymers, polyamides (nylons), polymethyl methacrylates and polyvinyl butyral etc. These polymers may be used individually or in the form of mixtures of two or more thereof.

The polymer barrier layer thickness is normally within the range from about 0.1 $\mu$m to about 6 $\mu$m, and a thickness within the range from about 0.2 $\mu$m to about 3 $\mu$m is especially desirable. A polymer barrier layer can be provided by coating a solution of the polymer in an organic solvent and drying in accordance with the methods disclosed in Japanese Patent Application (OPI) No. 19,062/83 and Japanese Patent Application (OPI) NO. 21,452/85.

The use of an air barrier layer consisting of a membrane filter, or a membrane filter which has been treated to render it water repellent, consisting of a vinyl polymer such as polyethylene or polypropylene, or a fluorine containing vinyl polymer such as polytetrafluoroethylene etc. is preferred from the points of view of achieving an analytical procedure of short duration, a high degree of accuracy and a highly uniform coloration or change in color in the indicator layer.

The ammonia producing reaction layer (referred to below as the reaction layer) contains reagents which react with an ammonia producing substance and produce gaseous ammonia. It is provided directly, or on a tacky intermediate layer which is described below on the barrier layer. The reaction layer usually contains a reagent capable of reacting with an ammonia producing substance to produce ammonia (generally an enzyme or a reagent which contains an enzyme), an alkaline buffer for ensuring that the ammonia which is produced by the reaction is released efficiently as gaseous ammonia, and a hydrophilic polymer binder which can be formed into a film.

The reagent which reacts with the ammonia producing substance and produces ammonia is preferably an enzyme or a reagent which contains an enzyme, and an enzyme appropriate for the analysis can be selected readily for use according to the type of ammonia producing analyte. When an enzyme is used as the above mentioned reagent, the combination of ammonia producing substance and reagent is determined by the specificity of the enzyme. Specific examples of ammonia producing substance/reagent combinations include urea/urease, creatinin/creatinine deiminase, amino acids/amino acid dehydrogenase, amino acids/amino acid oxidase, amino acids/ammonialyase, amines/amine oxidase, diamines/amine oxidase, glucose and phosphoamidate/phosphamidate hexose phosphotransferase, ADP/carbamate kinase, acid amide/amide hydrolase, nucleobase/nucleobase deaminase, nucleoside/nucleoside deaminase, nucleotide/nucleotide deaminease, guanine/gluanase etc.

The alkaline buffers which can be used in the reaction layer have a pH within the range from about 7.0 to 10.5 and preferably within the range from about 7.5 to 10.0. Actual examples of buffers include ethylenediamine tetraacetic acid (EDTA), tris(hydroxymethyl)aminomethane (Tris), phosphate buffer, N,N-bis(2-hydroxyethyl)glycine (Bicine), N-[tris(hydroxymethyl)methyl]-3-aminopropane sulfonic acid (Taps), N-2-hydroxyethylpiperazine-N'-2-hydroxypropane-3-sulfonic acid, (Heppso), N-2-hydroxyethylpiperazine-N'-3-propanesulfonic acid (Epps), N,N-bis(2-hydroxyethyl)-2-aminoethane sulfonic acid, 3-[N-bis(hydroxyethyl)-amino]-2-hydroxypropane sulfonic acid (Dipso), N-hydroxyethylpiperazine-N'-ethane sulfonic acid (Hepes), piperazine-N,N'-bis(2-hydroxypropane sulfonic acid) dihydrate (Popso), 3-[N-tris(hydroxymethyl)methyamino]-2 hydroxypropane sulfonic acid (Tapso), N-tris(hydroxymethyl)methylamionoethane sulfonic acid (Tes), N-[2-hydroxy-1,1-bis(hydroxymethyl)-ethyl]glycine (Tricine) etc. or alkali metals salts (for example lithium salts, sodium salts, potassium salts etc.) or alkaline earth metal salts thereof. Details of these buffers are noted at pages 467-477 of *Biochemistry* Vol. 5 (1966); pages 300-310 of *Analytical Biochemistry*, Vol 104 (1980) and at pages 1312-1320 of the Japanese Chemical Society Publication entitles *Chemistry Handbook, Fundamentals Edition* ((Japanese), Tokyo, 1966, published by Maruzen Corp.).

A suitable hydrophilic polymer can be selected from among the water soluble binder polymers which can be used in the indicator layer described earlier. Other hydrophilic polymers which can be used in the reaction layer include gelatin, gelatin derivatives, agarose, pluran, pluran derivatives, polyvinyl alcohol, polyacrylamide etc. Of these polymers the use of gelatin or gelatin derivatives is generally preferred.

Wetting agents, binder crosslinking agents (hardening agents), stabilizers, heavy metal ion chelating agents (complexing agents) etc. may be included as required in the reaction layer, as well as the reagent which reacts with the ammonia producing substance and produces ammonia, the alkaline buffer and the hydrophilic polymer binder which can be made into a film. Suitable heavy metal ion chelating agents are those which can be used for masking heavy metal ions of the type which interfere with enzyme activity. Specific examples of such heavy metal ion chelating agents include complexanes such as EDTA.2Na, EDTA.4Na, nitrilotriacetic acid (NTA), diethylenetriamine penta-acetic acid etc.

The reaction layer may be formed by mixing the reagent which reacts with the ammonia producing substance and produces ammonia, the alkaline buffer and the above mentioned reagents which are added as required with the hydrophilic binder which can be formed into a film, such as gelatin etc. to form a coating liquid and then coating this liquid onto the barrier layer or a tacky intermediate layer and drying.

The amount of the reagent which reacts with the ammonia producing substance and produces ammonia included in the reaction layer is within the range from about 100 U to 10,000 U, and preferably within the range from about 200 U to 540 U, per square meter, in a case of using an enzyme. The use of an amount of alkaline buffer within the range from about 1% to 30 wt% with respect to the weight of binder is appropriate. Furthermore, when a heavy metal ion chelating agent is used, an appropriate amount is within the range from about 0.5% to 20% with respect to the weight of binder. The dry thickness of the reaction layer is normally within the range from about 1 $\mu$m to 20 $\mu$m and preferably within the range from about 3 $\mu$m to 10 $\mu$m.

The tacky intermediate layer which can be provided between the barrier layer and the reaction layer contains a polymer composition which is tacky in air at a humidity of from 10% to 85% and normal ambient temperature (from about 0° C. to about 40° C.). The tacky intermediate layer can be established using the material and procedure disclosed in Japanese Patent Application (OPI) No. 21,452/85. The polymer composition from which the tacky intermediate layer is made may be an individual, known polymer having a glass transition point ($T_g$) below 0° C., a mixture of two or more such polymers, or a mixture in which known tackifiers and surfactants have been added as required to such polymers or mixture thereof. The thickness of the tacky intermediate layer is normally within the range from about 0.1 $\mu$m to about 6 $\mu$m and preferably within the range from about 1 $\mu$m to about 4 $\mu$m.

Specific examples of polymers which can be used in a tacky intermediate layer include vinyl acetatebutylacrylate copolymers, poly(ethyl acrylate), styrene.butyl acrylate.acrylic acid.N-(hydroxymethyl)acrylamide four component copolymers, butyl acrylate.(ethylaceto-acetato)methacrylate.2-acrylamide-2-methyl propane sulfonic acid three component copolymers, etc.

The establishment of a tacky intermediate layer is preferred in cases where the polymer barrier layer consists of a thin, homogeneous non-porous, hydrophobic polymer (or a polymer which has limited hydrophilicity).

An ammonia diffusion preventing layer which as the function of essentially preventing the diffusion into the ammonia trapping layer of the ammonia which is produced in the ammonia producing reaction layer, and which essentially does not trap ammonia or give rise to an ammonia producing reaction, is provided on top of the ammonia producing reaction layer.

The ammonia diffusion preventing layer may be a layer which has other functions provided that it essentially does not trap ammonia or undergo an ammonia producing reaction. Examples of layers which have other functions include cured hydrophilic polymer layer, light shielding layer, bonding layer etc.

The polymer binders which can be used in the ammonia diffusion preventing layer can be selected without particular limitation, provided that they can be formed into essentially non-porous, water permeable films and laminated onto the reaction layer directly or by means of a suitable intermediate layer. Any of the polymer binders used in the aforementioned indicator or reaction layers can be used for this purpose, provided that they are essentially permeable to water. Of these polymers the use of a hydrophilic polymer, especially a water soluble hydrophilic polymer or one which is swelled by water, of the same type as used in the reaction layer is preferred. Preferred hydrophilic polymers are gelatin and gelatin derivatives.

A polymer binder can be used alone for the ammonia diffusion preventing layer, but its pH value is preferably adjusted between about 7.0 and about 11.0 by means of a suitable buffer in order to increase the efficiency with which the diffusion of ammonia is prevented. A pH value within the range from about 8.0 to about 10.0 is especially desirable.

Buffers may be selected without particular limitation for the buffering function for maintaining the pH value of the ammonia diffusion preventing layer within the aforementioned range, provided that they have a buffering function within the above mentioned pH range. Specific examples of buffers which can be used in an ammonia diffusion preventing layer include alkalines and alkaline buffers of the same type as used in the reaction layer described earlier, or the endogenous ammonia trapping layer described hereinafter.

A thicker ammonia diffusion preventing layer is preferred from the point of view of preventing the diffusion of the ammonia, but a thinner film is preferred from the point of view of water permeation, and a film thickness within a range which satisfies both of these functions is selected.

When the ammonia diffusion preventing layer is an essentially non-porous layer which contains a hydrophilic polymer binder, its thickness is normally within the range from about 5 $\mu$m to about 50 $\mu$m and preferably within the range from about 7 $\mu$m to about 30 $\mu$m, and the covering weight of the polymer binder is within the range from about 4.0 grams to about 40 grams, and preferably within the range from about 5.5 grams to about 25 grams, per square meter of the multi-layer element.

An endogenous ammonia trapping layer which contains a reagent which acts on the ammonia (endogenous ammonia) which is present in the aqueous fluid sample and converts it into a form such that it does not reach the reaction layer below (referred to simply as the "endogenous ammonia trapping layer" is provided directly, or on an intermediate light shielding layer described hereinafter or some other type of intermediate layer, on top of the ammonia diffusion preventing layer. The endogenous ammonia trapping layer has the function of trapping endogenous ammonia which is also present in the sample before the ammonia producing substance such as creatinine or BUN etc. which is the analyte reaches the reaction layer and commences the reaction which produces the ammonia.

The term "trapping endogenous ammonia" signifies that a reagent system which is included in the endogenous ammonia layer binds with the endogenous ammonia, to assume a state from which it is essentially unable to dissociate during the period of the analytical procedure, or that the reagent system which is included in the endogenous ammonia trapping layer brings about a chemical reaction with the endogenous ammonia, convering the endogenous ammonia to some other chemical substance (in practice to an ammonium salt, ammonium ion or a chemical substance which is different from gaseous ammonia), so that the endogenous ammonia is fixed in the endogenous ammonia trapping layer and is essentially unable to reach the reaction layer. The latter type of endogenous ammonia trapping layer which contains a reagent system which has the function of reacting with and fixing the endogenous ammonia is preferred. In this specification the reagent systems which bring about a chemical reaction with the endogenous ammonia and convert it into a different chemical substance are referred to as endogenous ammonia trapping reagents.

Reagent compositions which contain enzymes with the ability catalytically to convert ammonia as a substrate to some other substance are preferred for the endogenous ammonia trapping reagent. Specific examples of endogenous ammonia trapping reagents include reagent compositions which contain NADH (the reduced form of nicotinamide adenine dinucleotide) and/or NADPH (the reduced form of nicotinamide adenine dinucleotide phosphate), gluatmic acid dehydrogenase (both EC1.4.1.4. and EC1.4.1.3. may be used, which are referred to below as "GLDH") and α-ketoglutaric acid or salts thereof, (referred to below as "α-KG"). Furthermoe, reagent compositions which contain aspartase (EC4.3.1.1) and fumaric acid or fumarates can also be used. The use of reagent compositions which contain NADH, GLCH and α-KG are preferably used for the endogenous ammonia trapping reagents in the integral multi-layer analysis elements of this invention. Furthermore, when reagent compositions which contain GLDH or reagent compositions which contain aspartase are used, the use of an appropriate buffer is preferred so as to maintain the pH value of the endogenous ammonia trapping layer normally below about 8.5 and preferably within the range from about 7.0 to 8.5.

Buffers for maintaining the aforementioned pH value which can be used in the endogenous ammonia trapping reagent include those disclosed at pages 1312–1320 of the Japanese Chemical Society Publication entitled *Chemistry Handbook, Fundamentals Edition* (Japanese) (Maruzen Co., Tokyo, 1966); disclosed in Norman E. Good et al., "Hydrogen Ion Buffers for Biological Research", Biochemistry 5 (2) pages 467–477 (1966) and those disclosed by R. M. C. Dawson et al *Data for Biochemical Research*, pages 467–508 (2nd ed., Oxford Clerendon Press, (1969) and in *Analytical Biochemistry* 104, 300–301 (1980). Furthermore, the organic acids or their alkali metal (or alkaline earth metal) salts which are used in the integral multi-layer analysis elements disclosed in Japanese Patent Application (OPI) No. 28,277/82, the basic polymers, acidic polymers and alkali metal (or alkaline earth metal) salts of acidic polymers which are used in the integral multi-layer analysis elements disclosed in Japanese Patent Application (OPI) Nos. 143,959/84 and 10,171/85 etc. and mixtures of these materials can be used as the above mentioned buffers.

Examples of preferred buffers from among these pH buffers include combinations of disodium hydrogen phosphate, 3-morpholinopropane sulfonic acid (MOPS, CAS Reg. No. [1132-61-2]) and sodium hydroxide, combinations of potassium dihydrogen phosphate and disodium hydrogen phosphate, combinations of disodium hydrogen phosphate and citric acid, combinations of boric acid, sodium chloride and borax combinations of potassium dihydrogen phosphate and sodium tetraborate and combinations of sodium tetraborate and an alkaline agent such as sodium hydroxyde, potassium hydroxide, etc. The endogenous ammonia trapping layer consisting of reagents such as the above mentioned endogenous ammonia trapping reagent and pH buffer etc. and hydrophilic polymer binder which can be formed into a film. The hydrophilic polymer binders used in the above mentioned reaction layer can be used as hydrophilic polymer binders. In general, the use of gelatin and gelatin derivatives from among these polymer binders is preferred.

The thickness of the endogenous ammonia trapping layer is normally from about 3 $\mu$m to about 30 $\mu$m and preferably from about 5 $\mu$m to about 20 $\mu$m.

The endogenous ammonia trapping layers preferably contain NADPH of NADH, $\alpha$-ketoglutaric acid ($\alpha$-KG) and glutamic acid dehydrogenase (GLDH). The preferred range (per square meter of endogenous ammonia trapping layer) and preferred content range of these components are indicated below.

|  | Preferred Range (/m$^2$) | Content Range* |
|---|---|---|
| NADPH or NADH | about 1,000– about 2,000 mg | about 80– about 3,000 mg |
| $\alpha$-KG | about 1,500– about 4,000 | about 400– about 8,000 |
| GLDH | about 30,000– about 100,000 U | about 10,000– about 150,000 U |

*Coating amount (content) per square meter

Moreover, in cases where the endogenous ammonia trapping layer contains aspartase and fumaric acid (this may be in the form of a fumarate) the layer preferably contains at least 1000 units/m$^2$ of aspartase and at least 200 mg/m$^2$ of fumaric acid (and/or fumarate).

The endogenous ammonia trapping layer may consist of a fine porous layer in which an ammonia trapping reagent, pH buffer and a hydrophilic polymer which are used together as required, as contained in a porous spreading layer or in a fine porous layer which is established between a porous spreading layer and the ammonia diffusion preventing layer, rather than being as essentially non-porous layer which contains a polymer binder which is provided on top of the ammonia diffusion prevention layer as described above. When the ammonia trapping reagents are contained in a porous spreading layer, then the spreading layer also functions as an endogenous ammonia trapping layer. The amount of ammonia trapping reagent (covering weight), the type and amount (covering weight) of pH buffer and the pH value range of a fine porous endogenous ammonia trapping layer are the same as those in the essentially non-porous layer which contains a polymer binder. Bonding between an endogenous ammonia removing layer of fine porosity and a porous spreading layer is preferably achieved using the porous bonding technique disclosed in Japanese Patent Application (OPI) No. 4,959/86.

The light shielding layers which can be provided between the barrier layer and the endogenous ammonia trapping layer are water permeable or water penetrable layer in which fine particles or fine powders (referred to below simply as fine particles) which provide light shielding or light shielding and light reflecting properties are dispersed and retained in a small quantity of a hydrophilic (or weakly hydrophilic) polymer binder which can be formed into a film. The light shielding layer functions as a light reflecting and background layer as well as shielding the coloration of the aqueous fluid sample which has been spotted onto the porous spreading layer (described below) especially the red coloration due to hemoglobin when the sample consists of whole blood, when the detectable change (change in color, color forming buffer etc.) which is produced in the indicator layer is being measured by reflection from the support side.

Examples of fine particles which can be used to provide light shielding and light reflection include fine titanium dioxide particles, fine barium sulfate particles and fine particles or flakes of aluminum, etc.

Examples of hydrophilic (or weakly hydrophilic) polymer binders which can be fomred into films include gelatin, gelatin derivatives and polyacrylamide, etc. Mixtures of gelatin or gelatin derivatives with known hardening agents (crosslinking agents) can also be used.

The ratio of the fine light shielding particles and polymer binder (when dry) in the light shielding layer is normally within the range from about 2.5 to about 7.5 parts by volume (dry volume) of polymer binder per 10 parts by volume of fine light shielding particles and preferably within the range of from about 3.0 to about 6.5 parts by volume of polymer binder (dry volume) per 10 part by volume of the fine light shielding particles. When the fine light shielding particles consist of titanium dioxide, then the weight reatio is within the range of from about 0.6 to about 1.8 parts by weight (dry weight), and preferably within the range from about 0.8 to about 1.5 parts by weight (dry weight), of polymer binder per 10 parts by weight of fine titanium dioxide particles. The thickness of the dry light shielding layer is normally within the range from about 3 $\mu$m to 30 $\mu$m and preferably within the range from about 5 $\mu$m to about 20 $\mu$m.

A porous spreading layer may be provided as a separate layer on top of the endogenous ammonia trapping layer.

A woven material spreading layer as disclosed in Japanese Patent Application (OPI) Nos. 164,356/80 and 6,359/82 (for example a flat wave such as a broadcloth or poplin), a knitted material spreading layer as disclosed in Japanese Patent Application (OPI) No. 222,769/85 (for example tricot knitting, double tricot knitting, Milanese knitting etc.), a spreading layer consisting of a paper made by including organic polymer fiber pulps as disclosed in Japanese Patent Application (OPI) No. 148,250/82, a membrane filter (blush polymer layer) as disclosed in Japanese Patent Document No. 21,677/78 and U.S. Pat. No. 3,992,158 etc., a nonwoven isotropic porous spreading layer such as the continuous fine-pore porous layers in which polymer micro-beads, glass micro-beads or siliceous earth etc. are retained in a hydrophilic polymer binder, and a non-woven isotropic porous spreading layer consisting of a continous fine-pore porous layer in which polymer micro-beads are bonded together with point to point contact with a polymer adhesive which is not swelled by water (a layer with a three dimensional lattice-like particle structure) as disclosed in Japanese Patent Application (OPI) No. 90,859/80 etc. can be used for the porous spreading layer.

These layers can be made to function as endogenous ammonia trapping layers by including an ammonia trapping reagent and a pH buffer etc. within the porous spreading layer, but in these embodiments a fiber-based spreading layer such as a woven material spreading layer or a knitted material spreading layer is preferred from the point of view of retaining the reagent composition within the spreading layer.

Examples of methods for including reagent compositions which contain ammonia trapping enzymes in spreading layers include first providing a porous spreading layer on a coated layer, and then a coating aqueous or organic solvent solution which contains the reagent composition which includes an enzyme on the top of the spreading layer, as disclosed in Japanese Patent Application (OPI) Nos. 171,864/84, 222,769/85 and 222,770/85 etc.

The woven material base or knitted material base used for the porous spreading layer may be subjected on at least one side to a physical activation treatment such as a glow discharge treatment or a coronal discharge treatment as disclosed in Japanese Patent Application (OPI) Nos. 66,359/82; a treatment which renders it hydrophilic such as a washing and decreasing treatment and immersion in a hydrophilic polymer etc. as disclosed in Japanese Patent Application Nos. 164,356/80 and 66,359/82 etc. or a treatment in which the base region is rendered hydrophilic by carrying out suitable combinations of these treatments, and the strength of adhesion with the underlying layer (on the side nearer to the support) can be increased in this way.

An essentially non-porous endogenous ammonia trapping layer which contains a hydrophilic polymer binder can also function as a bonding layer for the attachment of the porous spreading layer directly (i.e., without the establishment of a separate binding layer), but a known bonding layer containing a hydrophilic polymer as typified by gelatin can be provided with a view to bonding firmly and unifying the spreading layer. The thickness of the bonding layer, when dry, is within the range from about 0.5 $\mu$m to about 5 $\mu$m.

Surfactants can be included in the indicator layers, reaction layers, ammonia diffusion preventing layers, endogenous ammonia trapping layers, light shielding layers, bonding layers, spreading layers and spreading layers which contain ammonia trapping reagent compositions etc. Non-ionic surfactants are exmaples of such surfactants. Specific examples of such non-ionic surfactants include p-octylphenoxypolyethoxyethanol, p-nonylphenoxypolyethoxyethanol, polyoxyethylene oleyl ether, polyoxyethylenesorbitane monolaurate, p-nonylphenoxypolyglycidol, octylglucoside etc. The spreading action (metering action) on the aqueous fluid samples is improved by including a non-ionic surfactant in the spreading layer. The water in the aqueous fluid sample can be adsorbed with greater uniformity in the reagent layers or water absorbing layers during the analytical procedure by including a non-ionic surfactant in the layers, and furthermore the liquid contact with the spreading layer is speeded up and becomes essentially uniform.

The multi-layer analysis elements of this invention can be manufactured using known methods disclosed in the specifications of the various patent documents which have been referred to earlier.

The multi-layer analysis elements of this invention are preferably cut into rectangular pieces of side length about 15 mm and 30 mm or into circles of about the same size and housed in slide mounts as disclosed in Japanese Patent Publication No. 28,331/82, Japanese Utitlity Model Design Registration (OPI) No. 142,454/81, Japanese patent Application (OPI) No. 63,452/81, Japanese Utility Model Application (OPI) No. 32,350/83 and Republished Japanese Patent Application (based on International Application) No. 501,144/83 etc. from the points of view of manufacture, packaging, transportation, storage, and the making of measurements etc. Depending on the purpose for which they are used, these may be housed for use in the form of a long tape in cassette or magazine, or small pieces can be stuck onto or housed for use on a card which has a small opening.

The multi-layer analysis elements of this invention can be used for the analysis of analytes (ammonia producing substances) in fluid samples by following the procedures disclosed in the specifications of the various patenst mentioned previously. That is to say, an aqueous fluid sample of volume within the range of from about 5 $\mu$L ("L" is referred to "liter") to 30 $\mu$L and preferably within the range of from about 8 $\mu$L to 15 $\mu$L consisting of whole blood, plasma, lymph, urine etc. is spotted onto the spreading layer and incubated at an essentially constant temperature within the range from about 20° C. to about 40° C., and preferably at an essentially constant temperature in the vicinity of 37° C., for a period of from 1 minute to 10 minutes, and the analyte content of the fluid sample can be detemined on the basis of a conventional colorimatric method in which use is made of a previously prepared calibration curve by monitoring the light reflected from the optically transparent support side using visible or ultraviolet light of a wavelength the same as, or close to, the peak absorption wavelength of the color which has formed or changed within the element. Alternatively, the fluorescence intensity within the element can be measured and the analyte content of the fluid sample can be obtained using a calibration curve prepared beforehand. Quantitative analysis of the analyte can be carried out with a high degree of accuracy by setting the amount of fluid sample spoted and the time and temperature during incubating to constant levels. Amount of ammonia-producing substances which can be analyzed using the multi-layer analysis element of the invention is preferably from about 0.2 mg/dL to about 30 mg/dL in a case of creatinine and from about 5 mg/dL to about 200 mg/dL in a case of urea, in human blood. The measurements can be made very easily using chemical analysis apparatuses disclosed in Japanese patent Application (OPI) Nos. 125,543/85, 220,862/85, 294,367/86 and 161,867/83 etc. and highly accurate quantitative analysis can be achieved in this way.

EXAMPLE 1

An indicator layer was coated onto a transparent polyethyleneterephthalate (PET) film (thickness 180 $\mu$m) to provide the covering weights indicated below and, after drying, a polypropylene membrane filter (average pore size 0.2 $\mu$m), void fraction 75%, thickness 170 μm) was provided as an air barrier layer by applying a uniform pressure.

| Covering Weights (per square meter) of the Indicator Layer | |
| --- | --- |
| Bromophenol blue | 340 mg |
| Polyvinylacetate-ethylacrylate copolymer latex | 8.5 grams |
| N-polyoxyethylene-N-octanesulfonamide (containing average 16 units) | 100 mg |

A reaction layer, an ammonia diffusion preventing layer, an intermediate layer and an endogenous ammonia trapping layer were then coated in that order sequentially from aqueous solutions on top of the air barrier layer and dried to provide the covering weights indicated below in each case.

| Covering Weights (per square meter) of the Reaction Layer | |
| --- | --- |
| Alkali treated gelatin | 11.7 g |
| Sodium tetraborate | 1.7 g |
| p-Nonylphenoxypolyglycidol (average length 10 glycidol units) | 300 mg |
| Creatinene iminohydrolase (EC3.5.4.21) (Sodium hydroxide was added to adjust pH of coating solution to 9.5. Hereinafter, the pH value was adjusted in the same way.) | 750 U |

| Covering Weights (per square meter) of the Ammonia Diffusion Preventing Layer | |
| --- | --- |
| Dry Layer thickness | 7.5 μm |
| Alkali treated gelatin | 8.3 g |
| p-Nonylphenoxypolyglycidol (average length 10 glycidol units) | 200 mg |
| Sodium tetraborate (pH of the coating liquid 9.0) | 750 mg |

| Covering Weights (per square meter) of the Endogenous Ammonia Trapping Layer | |
| --- | --- |
| Alkali treated gelatin | 7.5 g |
| Sodium tetraborate | 1.35 g |
| p-Nonylphenoxypolyglycidol (average length 10 glycidol units) | 170 mg |
| u-ketoglutaric acid | 2.5 g |
| NADPH | 1.6 g |
| GLDH (EC.1.4.1.4) (pH of the coating liquid 8.0) | 70000 U |

The endogenous ammonia trapping layer was uniformly swelled using a 0.2% aqueous p-nonylphenoxypolyglycidol solution and then a tricot knitted cloth (about 240 μm thick using polyethylene terephthalate spinning yarn, gauge No. 40, given a 25% weight reduction treatment in NaOH) which had been subjected to a glow discharge was adhered and passed between pressure rollers to form a uniform laminate.

An integral multi-layer analysis element for the quantitative analysis of creatinine was completed by dipcoating in the following solution to provide the coating weights indicated below and drying, in order to improve the spreading properties of this laminated element.

| | |
| --- | --- |
| Methylcellulose (2% aqueous solution of viscosity 50 cps at 20° C.) | 800 mg |
| Hydroxypropylcellulose (containing 28–30% methoxy groups, 7–12% hydroxypropoxy groups, 2% aqueous solution of viscosity 50 cps at 20° C.) | 800 mg |
| Fine titanium dioxide grains (rutile type, trains size 0.25–0.40 μm) | 10.7 g |
| Nonylphenoxypolyethoxyethanol (containing average 40 ethoxy units) | 2.0 g |

| -continued | |
| --- | --- |
| p-Nonylphenoxypolyglycidol (average length 10 glycidol units) | 220 mg |

EXAMPLE 2

An integral multi-layer analysis element for the quantitative analysis of creatinine was prepared in the same way as in Example 1 except that the covering weights of the components in the ammonia diffusion preventing layer were changed in the way indicated below.

| Covering Weights (per square meter) of the Ammonia Diffusion Preventing Layer | |
| --- | --- |
| Dry layer thickness | 15 μm |
| Alkali treated gelatin | 16.6 g |
| p-Nonylphenoxypolyglycidol (average length 10 glycidol units) | 400 mg |
| Sodium tetraborate (pH of the coating liquid 9.0) | 1500 mg |

EXAMPLE 3

An integral multi-layer analysis element for the quantitative analysis of creatinine was prepared in the same way as in example 1, except that the covering weights of the components in the endogenous ammonia trapping layer were changed in the way indicated below.

| Covering Weights (per square meter) of the Endogenous Ammonia Trapping Layer | |
| --- | --- |
| Alkali treated gelatin | 7.5 g |
| Sodium tetraborate | 1.35 g |
| p-Nonylphenoxypolyglycidol (average length 10 glycidol units) | 170 mg |
| Sodium α-ketoglutarate | 2.5 g |
| NADH | 160 mg |
| Adenosine diphosphate (ADP) | 560 mg |
| GLDH (EC.1.4.1.4) (pH of the coating liquid 8.0) | 10500 U |

COMPARATIVE EXAMPLE 1

An integral multi-layer analysis element for the quantitative analysis of creatinine was prepared in the same way as in example 1, except that the endogenous ammonia trapping layer was provided directly on top of the reaction layer without an ammonia diffusion preventing layer.

COMPARATIVE EXAMPLE 2

An integral multi-layer analysis element for the quantitative analysis of creatinine was prepared in the same way as in Example 3, except that the endogenous ammonia trapping layer was provided directly on top of the reaction layer without an ammonia diffusion preventing layer.

The five integral multi-layer analysis elements for the quantitative analysis of creatinine described above were evaluated using the method indicated below. Evaluation test solutions were prepared by dissolving creatinine crystals in a 7% aqueous human serum albumin solution to provide final concentrations of 1, 2, 4, 8 and 16 mg/dL.

Ten microliters of the evaluation test solution was spotted onto the spreading layer of each analysis element, and the color optical density was measured by means of reflected light using visible light of middle wave length 600 nm after 6 minutes. The numerical values shown in Tables 1 and 2 are the values obtained as the difference between the color optical density when each evaluation test solution was dropped onto the element and the color optical density obtained when the same albumin solution which did not contain creatinine was dropped onto the element.

The results obtained when NADPH was used as coenzyme in the endogenous ammonia trapping layer are shown in Table 1, and it is clear that the integral multi-layer analysis elements for the analysis of creatinine shown as Example 1 and 2 gave higher color optical densities than comparative example 1 which had no ammonia diffusion preventing layer. The unfied multi-layer analysis elements of examples 1 and 2 and comparative example 1 were such that endogenous ammonia had no effect on the color optical density when included in concentrations of up to about 600μg/dL.

TABLE 1

| Creatinine Concentration (mg/dL) | Multi-layer Analysis Element | | |
|---|---|---|---|
| | Example 1 | Example 2 | Comparative Example 1 |
| 1 | 0.016 | 0.024 | 0.010 |
| 2 | 0.039 | 0.061 | 0.024 |
| 4 | 0.092 | 0.129 | 0.075 |
| 8 | 0.198 | 0.232 | 0.167 |
| 16 | 0.348 | 0.396 | 0.294 |
| Thickness of the Ammonia Diffusion Preventing Layer | 7.5 μm | 15 μm | None |

(The numerical values in the Table are color optical densities.)

The results obtained using NADH as a co-enzyme in the endogenous ammonia trapping layer are shown in table 2, and it is clear that the integral multi-layer analysis element for the analysis of creatinine of example 3 provided a higher color optical density than comparative example 2 which did not have an ammonia diffusion preventing layer.

Moreover, the integral multi-layer analysis elements for creatinine analysis of example 3 and comparative example 2 were such that the color optical density was unaffected by the presence of endogenous ammonia in concentrations of up to about 200 μg/dL.

TABLE 2

| Creatine Concentration (md/dL) | Multi-layer Analysis Element | |
|---|---|---|
| | Example 3 | Comparative Example 2 |
| 1 | 0.059 | 0.038 |
| 2 | 0.133 | 0.085 |
| 4 | 0.205 | 0.167 |
| 8 | 0.146 | 0.351 |
| 15 | 0.726 | 0.623 |
| Thickness of the Ammonia Diffusion Preventing layer | 7.5 μm | NONE |

EXAMPLE 4

An integral muilti-layer analysis element for the quantitative analysis of creatinine having an indicator layer, an air barrier layer, a reaction layer, an intermediate layer, an endogenous ammonia trapping layer and a spreading layer containing knitted cloth on a color less transparent PET film support in this order, was prepared in the same way as in Example 1.

| Covering Weights (per square meter) of the Reaction Layer | |
|---|---|
| Alkali treated gelatin | 10.0 g |
| Sodium tetraborate | 2.5 g |
| p-Nonylphenoxypolyglycidol (average length 10 glycidol units) | 230 mg |
| Creatinine iminohydrolase (adjusting pH of the Coating liquid 9.5 using NaOH) | 1125 U |

| Covering Weights (per square meter) of the Spreading Layer | |
|---|---|
| Methylcellulose 2% aqueous solution of viscosity 50 cpt at 20° C.) | 1100 mg |
| Hydroxypropylcellulose (containing 28-30% methoxy groups, 7-12% hydroxypropoxy groups, 2% aqueous solution of viscosity 50 cps at 20° C.) | 1100 mg |
| Fine titanium dioxide grains (rutile type, grain size 0.25-0.4 μm) | 14.9 g |
| Nonylphenoxypolyethoxyethanol (containing average 40 ethoxy units) | 2670 mg |
| p-Nonylphenoxypolyglycidol (average length 10 glycidol units) | 590 mg |

A quantitative analysis of creatinine was carried out using the integral multi-layer analysis element in the same way as in Example 1 and the same results as in Example 1 were obtained.

While the invention has been described in detail and with reference to specific embodiments thereof, it will be apparent to one skilled in the art that various changes and modifications can be made therein without departing from the spirit and scope thereof.

What is claimed is:

1. A multi-layer analysis element comprising an endogenous ammonia trapping layer, an ammonia producing layer comprising a reagent capable of reacting with an ammonia producing substance to produce gaseous ammonia, and at least one layer essentially incapable of trapping ammonia and essentially incapable of producing ammonia and capable of preventing the diffusion of gaseous ammonia, disposed between said endogenous ammonia trapping layer and said ammonia producing layer.

2. A multi-layer analysis element as claimed in claim 1 wherein the thickness of said layer capable of preventing the diffusion of ammonia is at least about 5 μm.

3. A multi-layer analysis element as claimed in claim 1 comprising an optically transparent and water impermeable support having thereon in the following order outwardly from said support:
    (1) An ammonia indicator layer comprising indicator capable of undergoing detectable change produced by gaseous ammonia;
    (2) A liquid permeation barrier layer permeable to gaseous ammonia;
    (3) Said ammonia producing layer;
    (4) Said layer capable of preventing the diffusion of ammonia;
    (5) Said endogenous ammonia trapping layer, wherein said endogenous ammonia trapping layer is also a porous spreading layer.

4. A multi-layer analysis element as claimed in claim 1 comprising an optically transparent and water impermeable support having thereon in the following order outwardly from said support:

(1) An ammonia indicator layer comprising an indicator capable of undergoing a detectable change produced by gaseous ammonia;
(2) A liquid permeation barrier layer permeable to gaseous ammonia;
(3) Said ammonia producing layer;
(4) Said layer capable of preventing the diffusion of gaseous ammonia;
(5) Said endogenous ammonia trapping layer; and
(6) a porous spreading layer.

5. The multi-layer analysis element as claimed in claim 4, wherein said liquid permeation barrier layer is a porous air barrier layer or a polymer barrier layer.

6. The multi-layer analysis element as claimed in claim 4, wherein said layer capable of preventing the diffusion of ammonia comprises from about 4.0 g/m$^2$ to 40 g/m$^2$ of an essentially non-porous, polymer binder, said layer having a thickness of from about 5 $\mu$m to 50 $\mu$m and a pH of from about 7.0 to 11.0.

7. The multi-layer analysis element as claimed in claim 4, wherein said layer capable of preventing the diffusion of ammonia comprises from about 5.5 g/m$^2$ to 25 g/m$^2$ of a hydrophilic polymer binder selected from a gelatin and a gelatin derivative, said layer having a pH of from about 8.0 to 10.0 and a thickness of from about 7 $\mu$m to 30 $\mu$m.

* * * * *